United States Patent [19]
Cebalo

[11] 3,990,881
[45] Nov. 9, 1976

[54] 5-(HETERO-RING SULFAMOYL)-1,3,4-THIADIAZOL-2-YLUREAS

[75] Inventor: Tony Cebalo, Indianapolis, Ind.

[73] Assignee: Eli Lilly and Company, Indianapolis, Ind.

[22] Filed: Aug. 25, 1975

[21] Appl. No.: 607,850

[52] U.S. Cl. .............................. 71/90; 260/293.68; 260/294.8 D; 260/306.8 D
[51] Int. Cl.² ....................................... C07D 285/12
[58] Field of Search ............. 260/306.8 D, 294.8 D, 260/293.68; 71/90

[56] References Cited
UNITED STATES PATENTS 3,726,892  4/1973  Cebalo ........................ 260/306.8 D

FOREIGN PATENTS OR APPLICATIONS

| 767,177 | 5/1971 | Belgium ...................... 260/306.8 D |
| 691,559 | 3/1969 | South Africa ................ 260/306.8 D |
| 1,230,432 | 5/1971 | United Kingdom .......... 260/306.8 D |
| 1,254,468 | 11/1971 | United Kingdom .......... 260/306.8 D |
| 1,290,223 | 9/1972 | United Kingdom .......... 260/306.8 D |
| 1,340,267 | 12/1973 | United Kingdom .......... 260/306.8 D |

*Primary Examiner*—Richard J. Gallagher
*Attorney, Agent, or Firm*—Dwight E. Morrison; Everet F. Smith

[57] ABSTRACT

Novel 1,3,4-thiadiazol-2-ylureas characterized by an hetero-ring sulfamoyl group at the 5-position, and by small alkyl or alkoxy groups on the urea nitrogens. The hetero-ring groups are 5- and 6-membered rings containing an oxygen, sulfur, or nitrogen atom, and may optionally be linked to the sulfamoyl nitrogen by a methylene group. The novel compounds are effective pre- and postemergence herbicides.

14 Claims, No Drawings

5-(HETERO-RING SULFAMOYL)-1,3,4-THIADIAZOL-2-YLUREAS

BACKGROUND OF THE INVENTION

1. Field of the Invention

This invention belongs to the field of agricultural chemistry and provides to the art new herbicides and herbicidal methods. Herbicides are now commonly used in the culture of virtually every crop and ornamental plant. It has been proved again and again that the proper use of herbicides for the elimination of weeds is necessary to maximize production. Appropriately chosen herbicides free the crop from the competition of weeds for the available water, nutrients and sunlight. Herbicides, when properly used, produce benefits in absolute yield and in economic profit which far outweigh the expense of the chemicals.

2. Description of the Prior Art

The 1,3,4-thiadiazol-2-ylureas as a group have been the subject of research in agricultural chemistry, and have been used as herbicides in the past. For example, British Pat. Specification No. 1,290,223, published Sept. 20, 1972, discloses thiadiazolylureas bearing a variety of substituents in the 5-position of the thiadiazole ring, none of which substituents contain the sulfamoyl moiety.

Another prior art reference is British Pat. Specification No. 1,230,432, published May 5, 1971, which teaches 1,3,4-thiadiazol-2-ylureas having alkyl, alkenyl, cycloalkyl, and alkylthio substituents attached at the 5-position of the thiadiazole ring.

British Pat. Specification No. 1,254,468, published Nov. 24, 1971, discloses 5-perfluoroalkyl-thiadiazolylureas.

Cebalo, South African Patent No. 69/1559, teaches 1,3,4-thiadiazolylureas bearing acyclic groups in the 5-position.

In addition, U.S. Pat. No. 3,726,892 (Apr. 10, 1973), teaches a number of 5-sulfamoyl-1,3,4-thiadiazol-2-ylureas alleged to have particular use as herbicides. This patent discloses a 5-morpholinosulfamoyl compound without specifically illustrating any activity for it.

Additional 5-sulfamoyl compounds, bearing various hydrocarbyl substituents on the sulfamoyl nitrogen, are disclosed by British Pat. Specification No. 1,340,267, published Dec. 12, 1973, as well as by Belgian Pat. No. 767,177.

SUMMARY OF THE INVENTION

This invention provides novel 1,3,4-thiadiazol-2-ylureas bearing an hetero-ring sulfamoyl group at the 5-position, which compounds are active as preemergence and postemergence herbicides. The 5- or 6-membered hetero-rings contain a single hetero-atom, which atom may be an oxygen, sulfur, or nitrogen atom, and the hetero-ring may optionally be linked to the sulfamoyl nitrogen atom via a methylene group.

The invention includes novel methods of using the compounds for the selective control of herbaceous weeds.

DESCRIPTION OF THE PREFERRED EMBODIMENT

This invention relates to novel compounds of the formula $$\begin{pmatrix} R \\ X \end{pmatrix}\!\!-\!(CH_2)_n-\overset{R^1}{\underset{|}{N}}-\overset{O}{\underset{\|}{S}}-\overset{N-N}{\underset{S}{\diagdown\!/}}-\overset{R^2}{\underset{|}{N}}-\overset{O}{\underset{\|}{C}}-N\!\!<\!\!\overset{R^3}{\underset{R^4}{}}$$

wherein

R combines with the carbon atom to which it is attached to form 1,1,4-butanetriyl, 1,1,5-pentanetriyl, 1,2,4-butanetriyl, 1,2,5-pentanetriyl, 1,3-butadiene-1,1,4-triyl, 1,3-butadiene-1,2,4-triyl, 3-butene-1,1,4-triyl, 1-butene-1,1,4-triyl, 1,3-pentadiene-1,1,5-triyl, 1,3-pentadiene-1,1-diyl-5-ylidene, 1,3-pentadiene-1,2-diyl-5-ylidene, 2,4-pentadiene-1,1,5-triyl, 2,4-pentadiene-1,2,5,-triyl, 1-pentene-1,1,5-triyl, 2-pentene-1,1,5-triyl, 3-pentene-1,1,5-triyl, 4-pentene-1,1,5-triyl, 1-pentene-1,2,5-triyl, 2-pentene-1,2,5-triyl, 3-pentene-1,2,5-triyl, or 4-pentene-1,2,5-triyl;

X is oxygen, sulfur, $$\diagdown\!\!\!\!NH, \text{ or } \diagdown\!\!\!\!N;$$

$n$ is 0 or 1;

$R^1$ is hydrogen, methyl, or ethyl;

$R^2$ and $R^3$ are the same or different, and are hydrogen or $C_1$-$C_3$ alkyl;

$R^4$ is $C_1$-$C_3$ alkyl or $C_1$-$C_3$ alkoxy.

A preferred group of compounds of the invention comprises those compounds of the above formula wherein $R^1$, $R^2$ and $R^4$ are methyl, $R^3$ is hydrogen or methyl, $n$ is 1, X is oxygen, and R, combined with the carbon atom to which it is attached, represents 1,1,4-butanetriyl, 1,3-butadiene-1,1,4-triyl, or 3-butene-1,1,4-triyl.

In the above generic formula, $C_1$-$C_3$ alkyl refers to methyl, ethyl, n-propyl, and isopropyl.

Also in the above formula, $C_1$-$C_3$ alkoxy refers to methoxy, ethoxy, n-propoxy, and isopropoxy.

It will be understood that a 5- or 6-membered heterocyclic ring (hetero-ring) is attached to the sulfamoyl nitrogen atom of the compounds, and that the ring may be optionally attached to that nitrogen atom through a linking methylene group. The hetero-rings, which contain either an oxygen, sulfur, or a nitrogen atom, are attached at the carbon atom at the 2- or 3-position of the hetero-ring. The hetero-rings may be saturated, or alternatively, may contain one, two, or three double bonds, where valence considerations permit.

The novel compounds of this invention are useful as preemergence and postemergence herbicides for inhibiting the growth of a variety of herbaceous weeds.

Compounds coming within the scope of the generic formula above, include, but are not limited to the compounds set forth hereinbelow:

1-ethyl-3-methoxy-3-methyl-1-[5-[N-methyl-N-(tetrahydro-2-pyranylmethyl)sulfamoyl]-1,3,4-thiadiazol-2-yl]urea 1-[5-[N-(2,3-dihydro-2-thenyl)-N-methylsulfamoyl]-1,3,4-thiadiazol-2-yl]-3-ethyl-3-methyl-1-propylurea 1-[5-[N-ethyl-N-(2-thenyl)sulfamoyl]-1,3,4-thiadiazol-2yl]-3,3-dimethyl-1-isopropylurea 3-[5-[N-(5,6-dihydro-2H-pyran-6-yl)-N-methylsulfamoyl]-1,3,4-thiadiazol-2-yl]-1-ethyl-3-isopropyl-1-propylurea 1-ethoxy-1-ethyl-3-propyl-3-[5-[N-(2H-pyran-6-yl)sulfamoyl]-1,3,4-thiadiazol-2-yl]urea 1-ethyl-3-isopropyl-1-[5-[N-methyl-N-(tetrahydrothio-2-pyranyl)sulfamoyl]-1,3,4-thiadiazol-2-yl]urea 1-[5-[N-(3,4-dihydro-2H-thiopyran-5-ylmethyl)sulfamoyl]-1,3,4-thiadiazol-2-yl]-1,3-diethyl-3-methylurea 1,3-dimethyl-1-[5-[N-(2-furyl)-N-methylsulfamoyl]-1,3,4-thiadiazol-2-yl]urea 1,1,3-trimethyl-3-[5-[N-(3-furyl)-N-ethylsulfamoyl]-1,3,4-thiadiazol-2-yl]urea 1-methyoxy-1-methyl-3-[5-[N-(2-furyl)-N-ethylsulfamoyl]-1,3,4-thiadiazol-2-yl]urea 1,3-dimethyl-1-[5-[N-(2,3-dihydro-2-thenyl)-N-methylsulfamoyl]-1,3,4-thiadiazol-2-yl]urea 1,3-dimethyl-1-propoxy-3-[5-[N-(2,3-dihydro-2-thienyl)sulfamoyl]-1,3,4-thiadiazol-2-yl]urea 1,1-diethyl-3-methyl-3-[5-[N-methyl-N-(4H-pyran-2-ylmethyl)sulfamoyl]-1,3,4-thiadiazol-2-yl]urea 1-ethyl-3-methyl-1-[5-[N-methyl-N-(tetrahydro-2-thienyl)sulfamoyl]-1,3,4-thiadiazol-2-yl]-3-propylurea 1-ethyl-1,3-dimethyl-3-[5-[N-(tetrahydro-2-furyl)sulfamoyl]-1,3,4-thiadiazol-2-yl]urea 1-[5-[N-ethyl-N-(3,4-dihydrofurfuryl)sulfamoyl]-1,3,4-thiadiazol-2-yl]-3-isopropoxy-1,3-dimethylurea 1-[5-[N-ethyl-N-(3-thenyl)sulfamoyl]-1,3,4-thiadiazol-2-yl]-1,3-dipropylurea 1-isopropyl-3-methyl-3-propyl-1-[5-[N-(tetrahydro-2-pyranyl)sulfamoyl]-1,3,4-thiadiazol-2-yl]urea 1-ethyl-3-[5-[N-ethyl-N-(tetrahydro-2-furyl)sulfamoyl]-1,3,4-thiadiazol-2yl]-1,3-dimethylurea 1-[5-[N-methyl-N-(2-thenyl)sulfamoyl]-1,3,4-thiadiazol-2-yl]-1,3,3-trimethylurea 1-ethyl-3-methyl-3-[5-[N-methyl-N-(2H-thiopyran-6-ylmethyl)sulfamoyl]-1,3,4-thiadiazol-2-yl]urea 1-ethyl-1-[5-[N-(2-furyl)-N-methylsulfamoyl]-1,3,4-thiadiazol-2-yl]-3-isopropyl-3-propylurea 1-ethyl-1-isopropyl-3-methyl-3-[5-[N-methyl-N-(tetrahydrothio-3-pyranylmethyl)sulfamoyl]-1,3,4-thiadiazol-2-yl]urea 1-isopropyl-3-methyl-3-propoxy-1-[5-[N-(tetrahydro-2-thienyl)sulfamoyl]-1,3,4-thiadiazol-2-yl]urea 1-[5-[N-(5,6-dihydro-2H-pyran-6-ylmethyl)sulfamoyl]-1,3,4-thiadiazol-2-yl]-1,3-dimethylurea 1,1-diisopropyl-3-methyl-3-[5-[N-(4H-pyran-2-yl)sulfamoyl]-1,3,4-thiadiazol-2-yl]urea 1-[5-[N-ethyl-N-(2,3-dihydro-2-furyl)sulfamoyl]-1,3,4-thiadiazol-2yl]-3-methoxy-1-methyl-3-propylurea 1-[5-[N-furfuryl-N-methylsulfamoyl]-1,3,4-thiadiazol-2-yl]-3-methyl-1-propylurea 1,3-dimethyl-1-[5-[N-methyl-N-(2-pyridylmethyl)sulfamoyl]1,3,4-thiadiazol-2yl]urea 1,3-dimethyl-1-[5-[N-methyl-N-(3-pyridylmethyl)sulfamoyl]-1,3,4-thiadiazol-2-yl]urea 1,1,3-trimethyl-3-[5-[N-methyl-N-(3-pyridylmethyl)sulfamoyl]-1,3,4-thiadiazol-2-yl]urea 1,3-dimethyl-1-[5-[N-methyl-N-(3-piperidylmethyl)sulfamoyl]-1,3,4-thiadiazol-3-yl]urea 1-methyl-3-[5-[N-methyl-N-(3-piperidylmethyl-sulfamoyl]-1,3,4-thiadiazol-2-yl]urea The preferred compounds are selected from the group consisting of 1,3-dimethyl-1-[5-(N-methyl-N-tetrahydrofurfurylsulfamoyl)-1,3,4-thiadiazol-2-yl]urea 1,1,3-trimethyl-3-[5-(N-methyl-N-tetrahydrofurfurylsulfamoyl)-1,3,4-thiadiazol-2-yl]urea 1-methyl-3-[5-(N-tetrahydrofurfurylsulfamoyl)-1,3,4-thiadiazol-2-yl]urea 1-methyl-3-[5-(N-methyl-N-tetrahydrofurfuryl-sulfamoyl)-1,3,4-thiadiazol-2-yl]urea, and 1-[5-(N-furfuryl-N-methylsulfamoyl)-1,3,4-thiadiazol-2-yl]-1,3-dimethylurea.

The compounds of this invention are made by processes which follow the known methods of preparation of thiadiazolylureas, as taught by, for example, Cebalo, U.S. Pat. No. 3,726,892, supra.

Each of the novel compounds of the invention is prepared starting with an appropriate 2-amino or 2-alkylamino-1,3,4-thiadiazole-5-thiol. Such starting compounds are readily obtainable or are readily prepared by known methods. The alkylamino group is then converted to the urea moiety of the final products, and the thiol is converted to the sulfamoyl moiety. These two conversions are done in separate steps, which steps may be performed in either order. The conversions are described hereinafter.

The urea moiety is formed by allowing the amino or alkylamino group to react with an alkyl isocyanate, when $R^3$ in the desired product represents hydrogen; or, when $R^4$ represents alkyl or alkoxy, with an appropriately substituted carbamoyl chloride, to form the product. The isocyanate reaction is most readily carried out in a solvent such as ethyl acetate at an elevated temperature, such as the reflux temperature of the reaction mixture. The reaction with a carbamoyl chloride goes readily in the presence of a strong base, such as sodium hydride, at approximately icebath temperature.

The sulfamoyl moiety is formed in two steps. First, a 5-sulfonyl chloride is prepared by suspending the starting thiol in glacial acetic acid or aqueous hydrochloric acid, and adding gaseous chlorine to the suspension. Second, the sulfonyl chloride so prepared is allowed to react with an appropriately substituted amine, for example, N-(2-furfuryl)-N-methylamine, in the presence of an acid scavenger, at room temperature, to yield the desired product.

It is thus clear that all of the starting compounds used in the reactions are readily obtained.

The syntheses of the intermediates useful in the preparation of the novel compounds of this invention are illustrated by the Preparations, which follow:

PREPARATION 1

2-Methylamino-5-[N-methyl-N-(tetrahydrofurfuryl)-sulfamoyl]-1,3,4-thiadiazole

Fifteen grams of 2-methylamino-1,3,4-thiadiazole-5-thiol was suspended in a solution of 20 ml. of concentrated hydrochloric acid in 66 ml. of water, with stirring. Gaseous chlorine was bubbled into the suspension at a rapid rate, with continued stirring. After about 8 minutes, the suspension began to grow very thick. The mixture was stirred very vigorously and the chlorine flow was continued until the suspension became saturated with chlorine. The reaction mixture was then filtered and the solids were washed, first with 10 percent aqueous sodium carbonate solution, and then with water. The yield was about 13.7 g. of 2-methylamino-1,3,4-thiadiazole-5-sulfonyl chloride, having a m.p. of about 127°–30° C. This intermediate product was used in the next step without further purification.

Fifteen grams of the sulfonyl chloride, prepared as above, was suspended in 130 ml. of tetrahydrofuran, and 8.05 g. of N-methyl-N-(tetrahydrofurfuryl)amine was added very slowly, with stirring, to the suspension. After the amine was added, a solution of 7.07 g. of triethylamine in 25 ml. of tetrahydrofuran was added dropwise with continued stirring, while the reaction mixture was kept cool in a cold water bath. The reaction mixture was stirred overnight at room temperature and poured into water. The aqueous mixture was extracted with ethyl acetate, and the extract was washed with water, dried over anhydrous sodium sulfate, and concentrated to dryness under vacuum. The residue was washed from the flask with hexane. The mixture was concentrated to dryness in vacuo, and the residue recrystallized from benzene. The product weighed abut 16.9 g. and had a melting point of about 89°–93° C. It was identified by NMR spectrum and elemental analyses as 2-methylamino-5-[N-methyl-N-(tetrahydrofurfuryl)sulfamoyl]-1,3,4-thiadiazole.

PREPARATION 2

1-Methyl-3-(5-chlorosulfonyl-1,3,4-thiadiazol-2-yl)urea

To a suspension in 145.4 g. of 2-amino-1,3,4-thiadiazole-5-thiol in 300 ml. of dimethylformamide there was added dropwise 68.5 g. of methyl isocyanate. The suspension cleared, the solution became very clear, and the temperature rose. A very viscous precipitate separated in about 2 minutes. Two hundred milliliters of dimethylformamide was added and the reaction mixture was stirred at ambient room temperature for about 2 hours. The reaction product mixture was filtered, water was added to the mother liquor, and the mother liquors filtered again. The combined solids thus obtained were washed with water and dried. The product weighed about 235.5 g., had a melting point of about 235°–237° C., and was identified as 1-methyl-3-(5-mercap-to-1,3,4-thiadiazol-2-yl)urea.

A suspension of 40 g. of the thiadiazol-2-ylurea (prepared above) in 960 ml. of 70 percent aqueous acetic acid was prepared, and chlorine was bubbled through sulfuric acid into the stirred suspension at a temperature of about 0°–5° C. for about 2 hours. The suspension lost its turbidity after about 1 hour. The reaction product mixture was worked up by adding water, causing a pecipitate to separate. The precipitate which was filtered off and washed with water and dried. The dried precipitate weighed about 37.7 g., and had a melting point of about 142°–44° C. It was identified as 1-methyl-3-(5-chlorosulfonyl-1,3,4-thiadiazol-2-yl)urea.

PREPARATION 3

2-Methylamino-5-[N-methyl-N-furfurylsulfamoyl]-1,3,4-thiadiazole

To a solution of 8.4 g. of 2-methylamino-1,3,4-thiadiazole-5-sulfonyl chloride (see Preparation 1) in 100 ml. of tetrahydrofuran, cooled to about 0° C., there was added dropwise 4.4 g. of methylfurfurylamine. After the addition had been completed, 4.1 g. of triethylamine was added to the mixture dropwise and the mixture was then stirred at ambient room temperature overnight. The reaction product mixture was filtered to remove any salt. The filtrate was concentrated to yield an oil. Water was added to the oil. A precipitate formed which was filtered off and dried. The precipitate weighed about 6.2 g. and had a melting point of about 109°–112° C. It was identified as 2-methylamino-5-[N-methyl-N-furfurylsulfamoyl]-1,3,4-thiadiazole. It was used without further purification in the preparation of some of the final products of the invention.

PREPARATION 4

2Methylamino-5-[N-methyl-N-(3-pyridylmethyl)sulfamoyl]-1,3,4-thiadiazole

To a solution of 8.5 of 2-methylamino-1,3,4-thiadiazole-5-sulfonyl chloride (see Preparation 1) in 200 ml. of tetrahydrofuran, cooled to about 0° C., there was added dropwise, 5.68 g. of methyl 3-pyridylmethylamine. After addition was complete, there was then added dropwise 4.04 g. of triethylamine. The reaction product mixture was then allowed to warm to room temperature and was stirred overnight at ambient room temperature. The reaction mixture was filtered to remove any salt. The filtrate was concentrated in vacuo to yield an oil. Water was added to the oil and the mixture was extracted several times with methylene dichloride. The combined extracts were concentrated in vacuo to yield a brown solid weighing about 5.7 g. and having a melting point of about 67°–80° C. The material was identified as 2-methylamino-5-[N-methyl-N-(3-pyridylmethyl)-sulfamoyl]-1,3,4-thiadiazole, and was used without further purification in the preparation of one of the final products of the invention.

The preparations of the novel compounds of this invention are illustrated by the following Examples:

EXAMPLE 1

1,3-Dimethyl-1-[5-(N-methyl-N-tetrahydrofurfurylsulfamoyl)-1,3,4-thiadiazol-2-yl]urea To a suspension of 4 g. of 2-methylamino-5-[N-methyl-N-tetrahydrofurfurylsulfamoyl]-1,3,4-thiadiazole (from Preparation 1) in 30 ml. of ethyl acetate there was added dropwise 2 ml. of methyl isocyanate. The reaction mixture was heated and stirred at reflux temperature overnight, and then concentrated to dryness in vacuo. The residue was removed from the flask with hexane and the hexane was evaporated in vacuo, leaving a residue. The residue was recrystallized from benzene to yield a product having a melting point of about 124°–126° C., and weighing about 3.5 g. The product was identified by NMR spectrum and elemental analyses as 1,3-dimethyl-1-[5-(N-methyl-N-tetrahydrofurfurylsulfamoyl)-1,3,4-thiadiazol-2yl]urea.

EXAMPLE 2

1-Methyl-3-[5-(N-tetrahydrofurfurylsulfamoyl)-1,3,4-thiadiazol-2-yl]urea

A suspension of 5 g. of 1-methyl-3-(5-chlorosulfonyl-1,3,4-thiadiazol-2-yl)urea (from Preparation 2) was prepared in 40 ml. of tetrahydrofuran. To this suspension was added very slowly 1.92 g. of tetrahydrofurfurylamine. There was then added dropwise a solution of 1.92 g. triethylamine in 5 ml. tetrahydrofuran. During this addition, the reaction mixture was kept cool in a cold water bath. The reaction mixture was stirred at ambient room temperature overnight. The reaction product mixture was then concentrated in vacuo, water was added, and the mixture acidified with aqueous hydrochloric acid. The precipitate which formed was filtered off and the solid obtained was washed with water. The solid was taken up in aqueous sodium hydroxide solution and the solution acidified with aqueous hydrochloric acid. The precipitate which formed was filtered off and washed with water and dried. The product thus obtained had a melting point of about 187°–190° C., and weighed about 2.02 g. The product was identified by elemental analyses as 1-methyl-3-[5-(N-tetrahydrofurfurylsulfamoyl)-1,3,4-thiadiazol-2-yl]urea.

EXAMPLE 3

1,1,3-Trimethyl-3-[5-(N-methyl-N-tetrahydrofurfurylsulfamoyl)-1,3,4-thiadiazol-2-yl]urea A solution was prepared of 5.84 g. of 2-methylamino-5-[N-methyl-N-tetrahydrofurfurylsulfamoyl]-1,3,4-thiadiazole (from Preparation 1) and 2.14 g. of N,N-dimethylcarbamoyl chloride in 40 ml. of dimethylformamide. The solution was cooled to about 0°–10° C., and 1 g. of sodium hydride (50 percent in oil) was added over a 40 minute period, with stirring. The reaction mixture was then allowed to warm to room temperature with continued stirring, and was stirred overnight at ambient room temperature. The mixture was then poured onto ice and the aqueous mixture thus formed was extracted with ethyl acetate. The ethyl acetate extract was washed with water, dried over anhydrous sodium sulfate, and concentrated in vacuo to an oil. The oil was extracted three times with hot hexane, decanting after each extraction. There was obtained 4.2 g. of an oil which was identified by NMR spectrum and elemental analyses as 1,1,3-trimethyl-3-[5-(N-methyl-N-tetrahydrofurfuryl-sulfamoyl)-1,3,4-thiadiazol-2-yl]urea.

EXAMPLE 4

1Methyl-3-[5-(N-methyl-N-tetrahydrofurfurylsulfamoyl)-1,3,4-thiadiazol-2-yl]urea To a solution of 5.1 g. of 1-methyl-3-(5-chlorosulfonyl-1,3,4-thiadiazol-2-yl)urea in 50 ml. of tetrahydrofuran, cooled to about 0° C. in an ice bath, there was added 2.3 g. of tetrahydrofurfurylmethylamine dropwise with stirring. After the addition had been completed, 2.02 g. of triethylamine was added dropwise, also with stirring. Stirring was continued while the temperature of the reaction mixture was maintained at about 0° C. for another hour. The reaction mixture was then allowed to warm to room temperature and was stirred overnight at ambient room temperature.

The reaction product mixture was filtered to remove any salt and the filtrate concentrated in vacuo to leave an oil. Water was added to the oil, causing a precipitate to form, and the precipitate was filtered off. Thin layer chromatography of a sample of the precipitate showed one spot. The precipitate weighed about 3.8 g., and was recrystallized from ethyl acetate to yield 2.4 g. of white crystals having a melting point of about 164°–165° C. The product was identified by elemental analyses and NMR spctrum as 1-methyl-3-[5-(N-methyl-N-tetrahydrofurfurylsulfamoyl)-1,3,4-thiadiazol-2-yl]urea.

EXAMPLE 5

1-[5-(N-Furfuryl-N-methylsulfamoyl)-1,3,4-thiadiazol-2-yl]-1,3-dimethylurea

To a solution of 3 g. of 2-methylamino-5-[N-methyl-N-furfurylsulfamoyl]-1,3,4-thiadiazole (from Preparation 3) in 50 ml. of toluene was added 1 g. of methyl isocyanate. The reaction mixture was heated at reflux for about 3 hours. The reaction product mixture was cooled and the solid which precipitated was filtered off. The solid weighed about 2.5 g. It was recrystallized from commercial absolute ethanol to give tan crystals weighing about 1 g., and having a melting point of about 131°–132° C. The product was identified by NMR spectrum and elemental analyses as 1-[5-N-furfuryl-N-methylsulfamoyl)-1,3,4-thiadiazol-2-yl]-1,3-dimethylurea.

EXAMPLE 6

1,3-Dimethyl-1-[5-[N-methyl-N-(3-pyridylmethyl)sulfamoyl]-1,3,4-thiadiazol-2-yl]urea To a solution of 5.7 g. of 2-methylamino-5-[N-methyl-N-(3-pyridylmethyl)sulfamoyl]-1,3,4-thiadiazole (from Preparation 4) in 100 ml. of toluene was added 3 g. of methyl isocyanate. The mixture was heated at reflux for about 5 hours. The mixture was cooled and concentrated in vacuo to yield a semisolid residue. A sample of the semisolid subjected to thin layer chromatography in ethyl acetate showed three spots. The semisolid was chromatographed on a silica gel column using ethyl acetate. The eluate corresponding to the second spot material was collected. The eluate was concentrated to dryness in vacuo, leaving a residue. The residue was recrystallized from ethyl acetate to yield white crystals having a melting point of about 169°–170° C., and weighing about 2.2 g. The product was identified by NMR spectrum and elemental analyses as 1,3-dimethyl-1-[5-[N-methyl-N-(3-pyridylmethylsulfamoyl]-1,3,4-thiadiazol-2-yl]urea.

The herbicidal properties of the novel compounds of this invention have been evaluated in controlled tests conducted in the greenhouse and in the field, as described hereinbelow.

Trial 1

A standard soil mixture was prepared consisting of one part masonry sand and one part shredded top soil blended together and then autoclaved. Postemergence and preemergence plantings were made in square, plastic containers measuring 6.7 cm. on a side at the top, 5.4 cm. on a side at the bottom, and having a height of 5.9 cm. Each container had 4 bottom holes for drainage. The containers were filled for planting as follows: 150 ml. of the standard soil mixture was placed in each container and tamped and leveled with a bench brush. The seeds were planted in individual rows. Some 6–12 tomato seeds (*Lycopersicon esculentum*) were planted in the middle row; 75–125 large crabgrass seeds (*Digitaria sanguinalis*), in one outside row; and 50–100 pigweed seeds (*Amaranthus retroflexus*) were planted in the other outside row. Twenty ml. of the soil mixture was then added by means of a sifter to each container, to cover the seeds. Approximately 30 ml. of a fertilizer solution containing 158 mg. of a soluble fertilizer (23-21-17) was added to each postemergence container one day before treatment.

Postemergence containers were planted 11–13 days prior to treatment. The postemergence containers were then placed under artificial lights in the growth room and given about 12–18 hours of light each day, depending upon the environmental conditions, and subjected to a temperature of about 74°–80° F. Preemergence containers were planted one day prior to treatment, and received no fertilizer.

The compounds to be tested were formulated in the following manner: To 20 mg. of the compound was added 1 ml. of solvent (1:1 ratio or acetone and ethyl alcohol containing Toximul R and S). A tissue grinder was used, if necessary, to aid in preparing the solution. The solution thus formed was diluted to 4 ml. with deionized water. The solvent was prepared by placing 1.174 g. of Toximul R and 0.783 gm. of Toximul S in 100 ml. of acetone and 100 ml. of ethyl alcohol. Toximul R and Toximul S are each identified as a sulfonate/nonionic blend, manufactured by Stepan Chemical Company, Northfield, Illinois.

The test formulations were applied with a modified DeVilbiss atomizer operated at a pressure of about 2-3 psi of air. Each container received 1.5 ml. of the solution containing the test material, resulting in an application rate of 16.8 kg./ha. Each compound was applied at this treatment rate to one pre- and one post-emergent container. There were also control containers which received no test compound.

After treatment, all the containers were placed in the greenhouse on the greenhouse tables, and watered as necessary. A plant respose or injury rating was made 10–13 days after treatment, depending upon the season. Each test plant species was rated as follows:

1 = no injury
2 = slight
3 = moderate
4 = severe
5 = death of plant or no seedling emergence The test results are set forth in Table 1, which follows. In the Table, column 1 lists the test compound, identified by the number of the operating example describing the synthesis of the compound; columns 2, 3, and 4 list the injury rating for the particular plant seedlings when test compound was applied preemergence; and columns 5, 6, and 7 list the injury ratings for the particular plant seedlings to which the test compounds were applied postemergence. The plant species are identified as follows:

J — Tomato
M — Large crabgrass
P — Pigweed

Table 1

| Example No. | 16.8 kg./ha. Preemergence | | | Postemergence | | |
|---|---|---|---|---|---|---|
| | J | M | P | J | M | P |
| 1 | 4 | 3 | 5 | 5 | 4 | 5 |
| 3 | 5 | 4 | 5 | 5 | 5 | 5 |
| Control | 1 | 1 | 1 | 1 | 1 | 1 |

Trial 2

Soil, prepared and sterilized in the same manner as described in Trial 1, was also used in this Trial. Plantings were made in galvanized metal flats which measured 31.5 cm. long, 21.5 cm. wide, and 8 cm. deep, with holes and grooves in the bottom for drainage. The standard planting procedure involved filling each flat about two-thirds full with the sterilized soil, and leveling and tamping the soil. For preemergence testing, two flats, each containing ten different species of plants were used. The seeds were planted in rows parallel to the long axis, one species per half row. After planting, the seeds are covered with about 0.5 to 1.0 cm. of sterilized soil. Preemergence flats were planted the same day the treatments were applied. The plant species used and the approximate number of seeds planted were as follows:

A—Corn (*Zea mays*) 4
B—Cotton (*Gossypium hirsutum*) 6
C—Soybean (*Glycine max*) 6
D—Wheat (*Triticum aesitivum*) 40
E—Alfalfa (*Medicago sativa*) 175
F—Sugar Beet (*Beta vulgaris*) 25
G—Rice (*Oryza sativa*) 35
H—Cucumber (*Cucumis sativus*) 8
J—Tomato (*Lycopersicon esculentum*) 45
K—Barnyardgrass (*Echinochloa crus-galli*) 100
L—Cocklebur (*Xanthium pensylvanicum*)
M—Large Crabgrass (*Digitaria sanguinalis*) 250
N—Mustard (*Brassica* sp.) 125
P—Pigweed (*Amaranthus retroflexus*) 250
Q—Foxtail Millet (*Setaria italica*) 100
R—Wild Oat (*Avena fatua*) 25
S—Velvetleaf (*Abutilon theophrasti*) 50
T—Morningglory (*Ipomoea purpurea*) 20
U—Zinnia (*Zinnia elegans*) 20
V—Lambsquarters (*Chenopodium album*) 100
W—Jimsonweed (*Datura stramonium*) 50

For the postemergence testing, a total of seven plant species were used. These were planted in rows perpendicular to the long axis of each flat, one species per row. The species and the number of seeds used were as follows:

A—Corn (*Zea mays*) 4
M—Large Crabgrass (*Digitaria sanguinalis*) 350
P—Pigweed (*Amaranthus retroflexus*) 350
Q—Foxtail Millet (*Setaria italica*) 200
S—Velvetleaf (*Abutilon theophrasti*) 100
T—Morningglory (*Ipomoea purpurea*) 25
U—Zinnia (*Zinnia elegans*) 20

After planting, the seeds were covered with about 0.5 to 1.0 cm. of sterilized soil. Postemergence flats were planted about 10–13 days prior to treatment and placed in the growth room until the day of treatment. In the growth room, the flats received about 12–18 hours of light a day, depending on light intensity, and were subjected to a temperature of about 74°–80° F. After treatment, all flats were removed to a greenhouse.

The compounds studied in the test were applied at rates ranging from 1.12 to 4.48 kg./ha. Each compound was formulated by dissolving it in a solvent, which solvent was prepared and had the same composition as described in Trial 1. The solution thus formed was diluted to the appropriate total volume with deionized water. This solution was then serially diluted with deionized water containing 0.1 percent of Toximul R and S to obtain the desired concentrations of compound.

The test formulations were applied with a modified DeVilbiss atomizer, using an air pressure of about 3–5 psi. Each flat received 12.5 ml. of solution.

After treatment, all the flats were transferred to the greenhouse for a period of about 12–14 days. The herbicidal effects were then rated on each plant species. The ratings were based on a 1-5 scale:

1 = no injury
2 = slight
3 = moderate
4 = severe
5 = death

The results from preemergence application of the test compounds are set forth in Table 2, which follows. In the Table, column 1 lists the test compound, identified by the number of the operating example describing the synthesis of the compound; column 2 lists the rate of application in kg./ha.; columns 3 through 23 list the injury ratings for the particular plant seedlings. Where more than one replicate was run, the average injury rating was recorded.

Trial 3

The compound of Example 3 was also tested in a field multiple crop screen, which was performed in a medium-heavy midwestern soil. Rows of the crops named in Table 4, below, were planted on a 50-cm. row spacing.

Table 2

Preemergence

| Compound of Example No. | Rate of Appln. kg./ha. | A | B | C | D | E | F | G | H | J | K | L | M | N | P | Q | R | S | T | U | V | W |
|---|---|---|---|---|---|---|---|---|---|---|---|---|---|---|---|---|---|---|---|---|---|---|
| 1 | 1.12 | 2 | 2 | 1 | 1 | 3 | 2 | 1 | 1 | 3 | 1 | 1 | 1 | 3 | 1 | 1 | 2 | 2 | 1 | 2 | *— | — |
|   | 2.24 | 3 | 3 | 1 | 3 | 3 | 3 | 1 | 3 | 4 | 3 | 1 | 3.5 | 4 | 2.5 | 3.5 | 3 | 4 | 2 | 4 | — | — |
| 3 | 2.24 | 2 | — | — | — | — | — | — | — | — | — | — | 2 | — | 2 | 2 | — | 2 | 2 | 2 | — | — |
| 4 | 8.96 | 1 | — | — | — | — | — | — | — | — | — | — | 3 | — | 2 | 3 | — | 2 | 1 | — | — | 3 |
| 5 | 1.12 | 1 | 1 | 1 | 2 | 4 | 4 | 1 | 2 | 1 | 1 | — | 2 | 2 | 4 | 2 | 2 | 4 | 2 | 5 | 3 | 3 |
|   | 2.24 | 1 | 1 | 1 | 2 | 5 | 4 | 2 | 3 | 4 | 5 | — | 4 | 4 | 3 | 3 | 3 | 4 | 4 | 5 | 3 | 4 |
|   | 4.48 | 2 | 2 | 3 | 4 | 5 | 4 | 2 | 4 | 4 | 4 | — | 3 | 5 | 5 | 5 | 5 | 5 | 5 | 5 | 5 | 4 |
| 6 | 4.48 | 1 | 1 | 2 | 1 | 1 | 1 | 1 | 1 | 1 | 1 | — | 3 | 2 | 2 | 2 | 1 | 4 | 1 | 1 | 3 | 1 |
|   | 8.96 | 2 | — | — | — | — | — | — | — | — | — | — | 4 | — | 2 | 2 | — | 5 | 4 | 5 | — | — |
| Controls | 0 | 1 | 1 | 1 | 1 | 1 | 1 | 1 | 1 | 1 | 1 | 1 | 1 | 1 | 1 | 1 | 1 | 1 | 1 | 1 | 1 | 1 |

*—indicates not run

The effects of the test compounds when applied postemergence to the test plants are recorded in Table 3, which follows. In the Table, column 1 lists the test compounds, identified as described above; column 2 lists the rate of application in kg./ha.; and columns 3 through 9 list the injury ratings for the particular plant seedlings. Where more than one replicate was run, the injury rating reported is an average figure.

The compound to be tested, formulated as a 120 g./liter emulsifiable concentrate, was applied postemergence as a spray of an aqueous dispersion. The dates when the crops were planted were staggered so that each crop had reached an appropriate size for postemergence application of a selective herbicide when the test compound was applied.

The test compound was applied as a 75-cm. band running perpendicularly to the rows of crops. Thus, each plot consisted of a 75-cm. length of a row of the crop. Applications were replicated and the results were averaged.

The plots were overseeded with foxtail millet and pigweed. Jimsonweed and velvetleaf were naturally occurring and were abundant enough to rate.

The injury to the crops and the weed control accomplished were rated twice, 11 days and 40 days, respectively, after application, although not all crops were rated at the 40 day time. Ratings were made by an experienced plant scientist and were expressed as percent injury to crops or percent control of weeds, as compared to untreated controls. The results are set forth in Table 4, which follows:

Table 3

Postemergence

| Compound of Example No. | Rate of Appln. kg./ha. | A | M | P | Q | S | T | U |
|---|---|---|---|---|---|---|---|---|
| 1 | 0.28 | 1 | 2 | 2 | 3 | 2 | 2 | 3 |
|   | 0.56 | 1.5 | 3.5 | 4.5 | 3.5 | 3.5 | 2.5 | 3.5 |
|   | 1.12 | 1.5 | 3.5 | 4 | 4.5 | 3.5 | 3 | 3.5 |
|   | 2.24 | 3.5 | 5 | 4.5 | 5 | 4.5 | 3.5 | 5 |
| 2 | 2.24 | 1 | 3 | 2 | 3 | 2 | 1 | 3 |
|   | 8.96 | 2 | 3 | 3 | 3 | 2 | 1 | 3 |
| 3 | 0.28 | 1 | 2 | 2 | 3 | 2 | 2 | 3 |
|   | 0.56 | 1.5 | 3 | 3.5 | 4 | 3 | 3 | 3.5 |
|   | 1.12 | 2 | 3.5 | 4 | 4 | 3 | 3.5 | 4.5 |
|   | 2.24 | 3 | 4 | 4.5 | 5 | 4.5 | 4 | 4.5 |
| 4 | 1.12 | 1 | 3 | 3 | 3 | 3 | 2 | 4 |
|   | 2.24 | 1 | 3 | 4 | 3 | 4 | 2 | 3 |
|   | 4.48 | 2 | 4 | 4 | 3 | 4 | 2 | 4 |
| 5 | 1.12 | 1 | 1 | 2 | 2 | 1 | 1 | 2 |
|   | 2.24 | 1 | 1 | 3 | 2 | 2 | 2 | 2 |
|   | 4.48 | 1 | 2 | 4 | 2 | 3 | 2 | 3 |
| 6 | 8.96 | 1 | 2 | 2 | 2 | 2 | 1 | 2 |
| Controls | 0 | 1 | 1 | 1 | 1 | 1 | 1 | 1 |

Table 4

Multiple Crop Screen
Percent Crop Injury

| | 11 days after treatment | | | | 40 days after treatment | | | |
|---|---|---|---|---|---|---|---|---|
| Crop | 0.56 kg./ha. | 1.12 kg./ha. | 2.24 kg./ha. | 4.48 kg./ha. | 0.56 kg./ha. | 1.12 kg./ha. | 2.24 kg./ha. | 4.48 kg./ha. |
| Sugarbeet | —* | 30 | 60 | 50 | — | — | — | — |
| Alfalfa | — | 40 | 30 | — | — | — | — | — |
| Tomato | 90 | 70 | 70 | 100 | — | — | — | — |
| Cabbage | 50 | 60 | 70 | 100 | — | — | — | — |
| Oat | 0 | 30 | 40 | 70 | — | — | — | — |
| Peanut | 30 | 30 | 40 | 70 | 40 | 30 | 50 | 60 |
| Wheat | 40 | 50 | 80 | 100 | — | — | — | — |
| Cucumber | — | 80 | 100 | 100 | — | — | — | — |
| Sorghum | 0 | 0 | 100 | 100 | 20 | 0 | 100 | 100 |
| Corn | 15 | 40 | 75 | 95 | 30 | 25 | 55 | 90 |
| Cotton | 90 | 90 | 100 | 100 | 30 | 60 | 100 | 100 |
| Bush Bean | 50 | 80 | 90 | 100 | 0 | 70 | 100 | 100 |
| Soybean | 70 | 90 | 90 | 100 | 20 | 30 | 100 | 100 |

Percent Weed Control

Table 4-continued

| | Multiple Crop Screen | | | | | | | |
|---|---|---|---|---|---|---|---|---|
| Foxtail Millet | 0 | 40 | 95 | 100 | 0 | 20 | 90 | 100 |
| Pigweed | 40 | 90 | 100 | 100 | 0 | 98 | 100 | 100 |
| Jimsonweed | 100 | 100 | 100 | 100 | 100 | 100 | 100 | 100 |
| Velvetleaf | 30 | 100 | 100 | 100 | 80 | 85 | 100 | 100 |

*—indicates not run.

The best use of the new compounds described herein is in the herbicidal method of selectively inhibiting the growth of herbaceous weeds, which method is an important embodiment of the present invention, and which comprises contacting the weeds with an herbicidally-effective amount of one of the new compounds. As has been demonstrated, the compounds and the method are herbicidally effective when the weeds are contacted either postemergence by direct contact with the weed, or preemergence, by contact of the treated soil with the weed seedling or with the germinating seed.

The usual range of application rates of the compounds is from about 0.05 to about 20 kg./ha. A preferred range is from about 1 to about 10 kg./ha. It will be understood that, due to unusual conditions of temperature, rainfall or soil organic matter, it will occasionally be necessary to use application rates either higher or lower than the range described here. In general, however, plant scientists will find that the compounds are most effective and economical when used at a rate in the described range. Of course, some weed species require higher application rates than others, as the examples illustrate.

It is not implied that all weeds growing in the treated area will be killed whenever one of the new compounds is applied thereto. The percentage of the weed population which will be killed depends on the age and vigor of the weeds at the time of application, the application rate, and the characteristics of the particular compound chosen. Those weeds which are not killed by the application will be injured to a greater or lesser degree depending on the same factors. Since the injury of weeds allows the crop to outgrow and shade out the weeds, merely injuring weeds confers a substantial benefit to the crop.

The novel compounds can be used as such or in the form of formulations comprising the active ingredient and various solid or liquid carriers. Examples of such formulations include wettable powders, emulsifiable concentrates, granule or pellet formulations, and the like.

Thus, the compounds can be formulated as concentrated compositions which are applied either to the soil or the foliage in the form of water dispersions or emulsions containing in the range of from about 0.1 percent to a few percent of the compound. Water-dispersible or emulsifiable compositions are either solids, usually known as wettable powders, or liquids, usually known as emulsifiable concentrates. Wettable powders comprise an intimate, finely-divided mixture of the thiadiazolylurea, an inert carrier, and surfactants. The concentration of the thiadiazolylurea in the wettable powder is usually from about 10 percent to about 90 percent. The inert carrier is usually chosen from among the attapulgite clays, the montmorillonite clays, the diatomaceous earths, or the purified silicates. Effective surfactants, comprising from about 0.5 percent to about 10 percent of the wettable powder, are found among the sulfonated lignins, the condensed naphthalenesulfonates, the naphthalenesulfonates, the alkylbenzenesulfonates, the alkyl sulfates, and nonionic surfactants, such as ethylene oxide adducts of phenol.

Typical emulsifiable concentrates of the new compounds comprise a convenient concentration of the thiadiazolylurea, such as from about 100 to about 500 g. per liter of liquid, dissolved in an inert carrier, which is a mixture of a water-immiscible solvent and emulsifiers. Useful organic solvents include the aromatics, especially the xylenes, and the petroleum fractions, especially the high-boiling naphthalenic and olefinic portions of petroleum. Many other organic solvents may also be used, such as the terpenic solvents, and the complex alcohols, such as 2-ethoxyethanol. Suitable emulsifiers for emulsifiable concentrates are chosen from the same types of surfactants as used for wettable powders.

When a thiadiazolylurea is to be applied to the soil, as for a preemergence application of the compound, it is convenient to use a granular or pellet formulation. Such a formulation typically comprises the compound dispersed on a granular inert carrier, such as coarsely ground clay. The particle size of granules usually ranges from about 0.1 to about 3 mm., while the pellets range in size from about 3 to 12 mm. The usual formulation process for granules comprises dissolving the compound in an inexpensive solvent and applying the solution to the carrier in an appropriate solids mixer. Somewhat less economically, the compound may be dispersed in a dough composed of damp clay or other inert carrier, which is then dried and coarsely ground to produce the desired granular product. Pellets are made by processing a powdered mix of carrier and compound in a pellet mill.

The usual agricultural chemical application equipment may be used for the application of formulations of the new compounds. Water-dispersed formulations are readily applied either to the soil or to foliage by means of sprayers which may be hand-carried, tractor-mounted, self-propelled, or towed. Granular formulations are applied by any of the many metering applicators which are in wide use. The operator of the application equipment need only take care to apply an amount of the formulation per unit area of land which supplies the desired application rate of the thiadiazolylurea, and to apply it evenly throughout the area to be treated.

I claim:
1. A compound of the formula

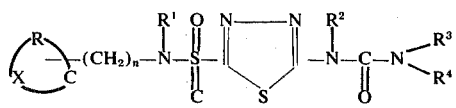

wherein
R combines with the carbon atom to which it is attached to form 1,1,4-butanetriyl, 1,1,5-pentanetriyl, 1,2,4-butanetriyl, 1,2,5-pentanetriyl, 1,3-butadiene-1,1,4-triyl, 1,3-butadiene-1,2,4-triyl, 3-butene-1,1,4-triyl, 1-butene-1,1,4-triyl, 1,3-pentadiene-1,1,5-triyl, 1,3-pentadiene-1,1-diyl-5-ylidene, 1,3-pentadiene-1,2-diyl-5-ylidene, 2,4-pentadiene-1,1,5-triyl, 2,4-pentadiene-1,2,5-triyl, 1-pentene-1,1,5-triyl, 2-pentene-1,1,5-triyl, 3-pentene-1,1,5-triyl, 4-pentene-1,1,5-triyl, 1-pentene-1,2,5-triyl, 2-pentene-1,2,5-triyl, 3-pentene-1,2,5-triyl, or 4-pentene-1,2,5-triyl;

X is oxygen, sulfur,

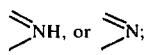

$n$ is 0 or 1;

$R^1$ is hydrogen, methyl, or ethyl;

$R^2$ and $R^3$ are the same or different, and are hydrogen or $C_1$—$C_3$ alkyl; and $R^4$ is $C_1$—$C_3$ alkyl, or $C_1$—$C_3$ alkoxy.

2. The compound of claim 1 which is 1-[5-(N-furfuryl-N-methylsulfamoyl)-1,3,4-thiadiazol-2-yl]-1,3-dimethylurea.

3. The compound of claim 1 which is 1-methyl-3-[5-(N-tetrahydrofurfurylsulfamoyl)-1,3,4-thiadiazol-2-yl]urea.

4. The compound of claim 1 which is 1-methyl-3-[5-(N-methyl-N-tetrahydrofurfurylsulfamoyl)-1,3,4-thiadiazol-2-yl]urea.

5. The compound of claim 1, which is 1,3-dimethyl-1-[5-[N-methyl-N-(3-pyridylmethyl)sulfamoyl]-1,3,4-thiadiazol-2-yl]urea.

6. A compound of claim 1, wherein $R^1$, $R^2$, and $R^4$ represent methyl, $R^3$ represents hydrogen or methyl, n represents 1, X represents oxygen, and R, combined with the carbon atom to which it is attached, represents 1,1,4-butanetriyl, 1,3-butadiene-1,1,4-triyl, or 3-butene-1,1,4-triyl.

7. The compound of claim 6 which is 1,3-dimethyl-1-[5-(N-methyl-N-tetrahydrofurfurylsulfamoyl)-1,3,4-thiadiazol-2-yl]urea.

8. The compound of claim 6 which is 1,1,3-trimethyl-3-[5-(N-methyl-N-tetrahydrofurfurylsulfamoyl)-1,3,4-thiadiazol-2-yl]urea.

9. A method of inhibiting the growth of herbaceous weeds which comprises contacting the weeds with an herbicidally-effective amount of a compound of claim 1.

10. The method of claim 9 wherein the amount of the compound is from about 0.05 kg./ha. to about 20 kg./ha.

11. The method of claim 10 wherein the compound is a compound of the formula

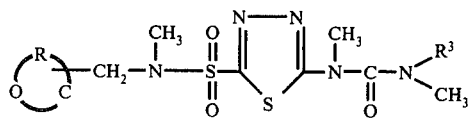

wherein $R^3$ represents hydrogen or methyl and $R_1$ combined with the carbon atom to which it is attached, represents 1,1,4-butanetriyl, 1,3-butadiene-1,1,4-triyl, or 3-butene-1,1,4-triyl- 12. The method of claim 11 wherein the compound is 1,3-dimethyl-1-[5-(N-methyl-N-tetrahydrofurfurylsulfamoyl)-1,3,4-thiadiazol-2-yl]urea.

13. The method of claim 11 wherein the compound is 1,1,3-trimethyl-3-[5-(N-methyl-N-tetrahydrofurfurylsulfamoyl)-1,3,4-thiadiazol-2-yl]urea.

14. The method of claim 11 wherein the compound is 1-[5-(N-furfuryl-N-methylsulfamoyl)-1,3,4-thiadiazol-2-yl]-1,3-dimethylurea.

* * * * *

United States Patent and Trademark Office

CERTIFICATE OF CORRECTION

PATENT NO. : 3,990,881
DATED : November 9, 1976
INVENTOR(S) : Tony Cebalo

It is certified that error appears in the above-identified patent and that said Letters Patent are hereby corrected as shown below:

Column 1, line 50, after "767,177" insert --Derwent No. 74859S--

Column 2, line 68, "2yl" should read -- 2-yl --.

Column 3, line 16, "methyoxy" should read --methoxy--.

Column 5, line 50, "pecipitate" should read --precipitate--.

Column 6, line 9, "2Methylamino" should read -- 2-Methylamino --

Column 7, line 37, "1Methyl" should read -- 1-Methyl --.

Column 15, lines 13-17 should read as follows:

-- $\geq$NH, or $\geq$N; --.

Column 16, line 28, "$R_1$" should read -- R, --.

Signed and Sealed this

Twenty-second Day of February 1977

[SEAL]

Attest:

RUTH C. MASON
Attesting Officer

C. MARSHALL DANN
Commissioner of Patents and Trademarks